(12) United States Patent
Gekhter

(10) Patent No.: US 8,394,011 B2
(45) Date of Patent: Mar. 12, 2013

(54) EXPANDABLE EXTERNAL PENILE SUPPORT DEVICE (EEPSD) WITH ATTACHMENTS AND METHOD OF MANUFACTURING

(75) Inventor: Vladimir Gekhter, Skokie, IL (US)

(73) Assignee: Global Life Technologies, LLC, Skokie, IL (US)

( * ) Notice: Subject to any disclaimer, the term of this patent is extended or adjusted under 35 U.S.C. 154(b) by 727 days.

(21) Appl. No.: 12/625,261

(22) Filed: Nov. 24, 2009

(65) Prior Publication Data
US 2010/0130816 A1 May 27, 2010

Related U.S. Application Data

(60) Provisional application No. 61/118,164, filed on Nov. 26, 2008.

(51) Int. Cl.
*A61F 5/00* (2006.01)

(52) U.S. Cl. .......................................... 600/39

(58) Field of Classification Search ............... 600/38–41
See application file for complete search history.

(56) References Cited

U.S. PATENT DOCUMENTS

| | | | | |
|---|---|---|---|---|
| 4,449,521 A | * | 5/1984 | Panzer | 600/39 |
| 5,800,340 A | * | 9/1998 | Gekhter et al. | 600/39 |
| 2007/0038019 A1 | * | 2/2007 | Weng | 600/38 |
| 2008/0076964 A1 | * | 3/2008 | Jared | 600/39 |

* cited by examiner

*Primary Examiner* — Samuel Gilbert
(74) *Attorney, Agent, or Firm* — Michael Best & Friedrich LLP

(57) ABSTRACT

The present invention relates to an expandable external penile support device (EEPSD) for use on a penis during sexual intercourse. The EEPSD includes a first support ring proximate a base of the penis, a latch pivotably coupled to the support ring, and a support member extending from the latch and defining a second support ring engageable with a distal end of the penis. The EEPSD expands and contracts to accommodate changes in penis size, usually due to the gain and loss of an erection.

14 Claims, 16 Drawing Sheets

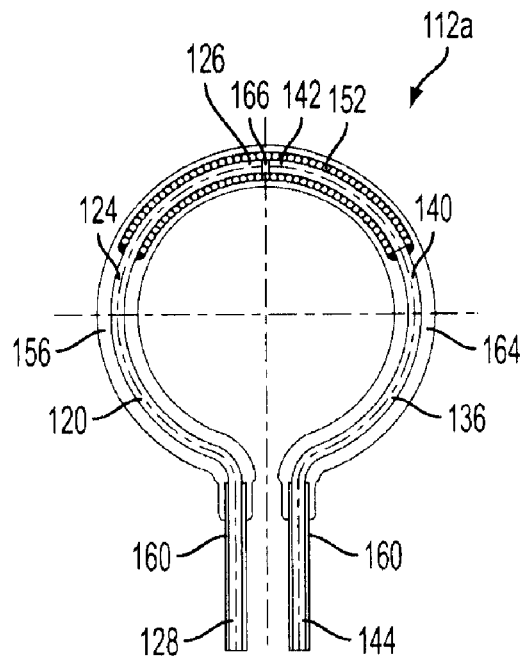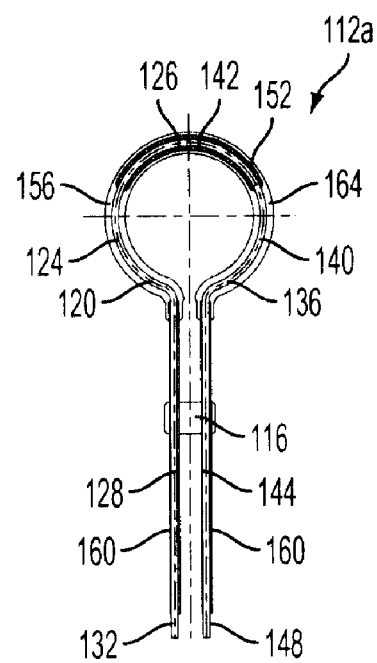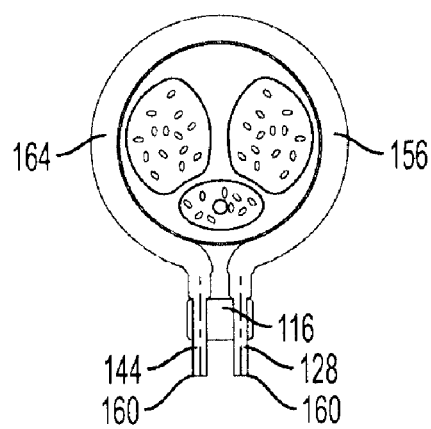

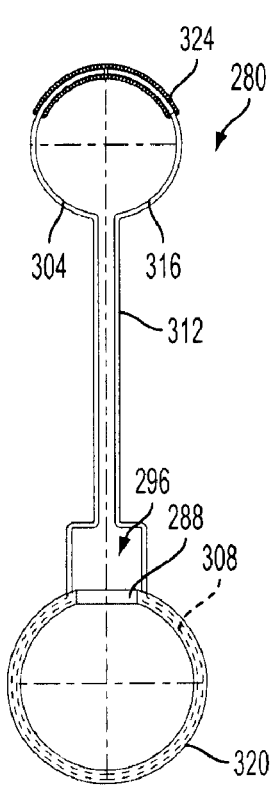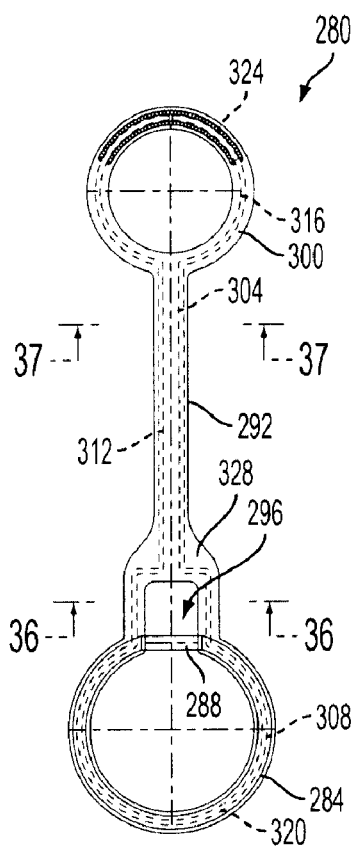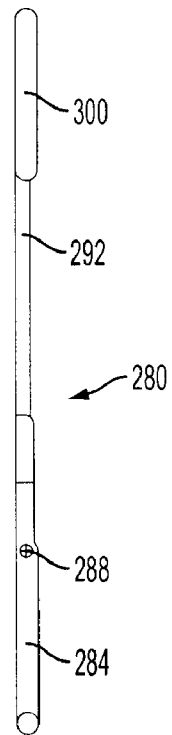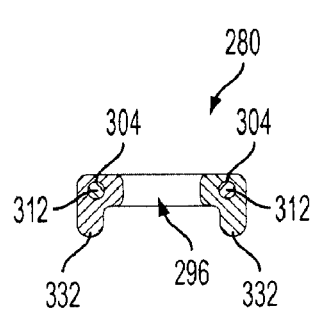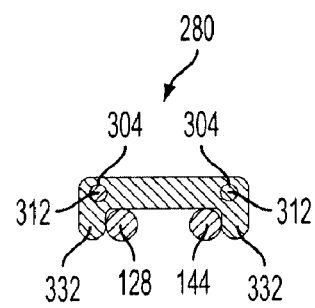
FIG. 33  FIG. 34  FIG. 35
FIG. 36  FIG. 37

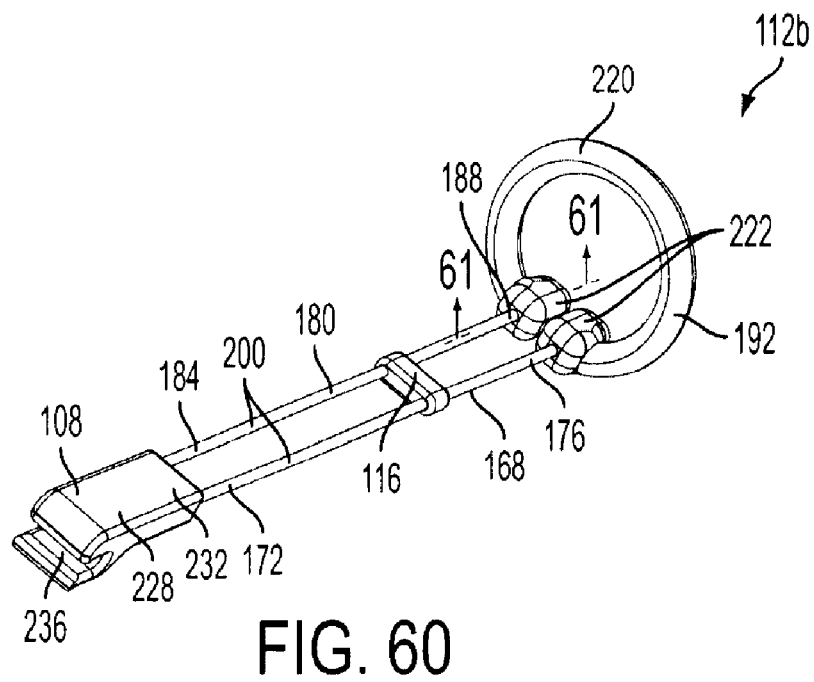
FIG. 60
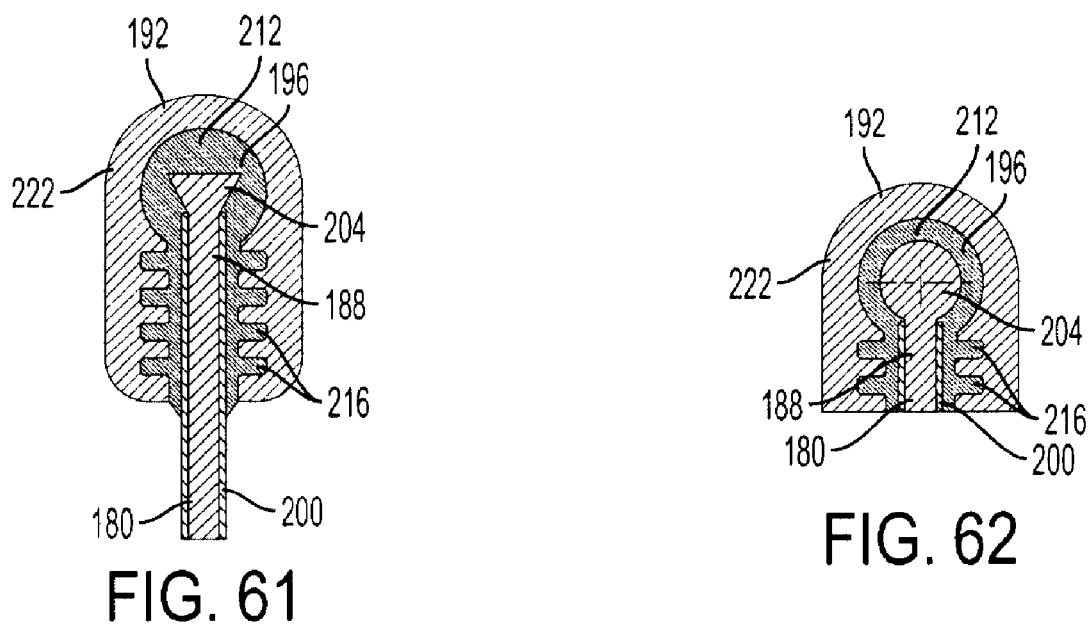
FIG. 61
FIG. 62

US 8,394,011 B2

EXPANDABLE EXTERNAL PENILE SUPPORT DEVICE (EEPSD) WITH ATTACHMENTS AND METHOD OF MANUFACTURING

CROSS-REFERENCE TO RELATED APPLICATION

This application claims the benefit of and priority to U.S. Provisional Patent Application No. 61/118,164 filed Nov. 26, 2008, the entire contents of which are hereby incorporated by reference.

FIELD OF INVENTION

The invention relates generally to sexual aids for men, and more particularly to the ability for men to perform intercourse with no or weak erection.

BACKGROUND OF INVENTION

Erectile dysfunction, sometimes called "impotence," is the repeated inability to get or keep an erection firm enough for sexual intercourse. "Impotence" may also be used to describe other problems that interfere with sexual intercourse and reproduction, such as lack of sexual desire and problems with ejaculation or orgasm. Erectile dysfunction, or ED, can be a total inability to achieve erection, an inconsistent ability to do so, or a tendency to sustain only brief erections. These variations make defining ED and estimating its incidence difficult. Estimates range from 15 million to 30 million men in the US and over 150 million men worldwide, depending on the definition used. The treatments for impotence include medications, vacuum devices, injectable drugs and implant surgeries. Perhaps the most publicized advance was the introduction of the oral drug sildenafil citrate (Viagra) in March 1998. Viagra fails to work for three out of 10 men, according to one published source or can not be used by 50% of men with erectile dysfunctions due to side effects according to other medical sources. In older men, ED usually has a physical cause, such as disease, injury, or side effects of drugs. Any disorder that causes injury to the nerves or impairs blood flow in the penis has the potential to cause ED. The frequency of impotence in men increases with age, about 5 percent of 40-year-old men and between 15 and 25 percent of 65-year-old men experience ED. Medications can produce many undesirable side effects including death. Vacuum devices are clumsy and inconvenient; surgeries are painful, ineffective, expensive and even dangerous.

Current external penile support devices do not find broad applications in treatment of impotence due to great discomfort for the users and difficulties to adjust for the variety of men's genitalia. Another problem with existing external penile support devices is that they include a number of parts which often become disassembled during use, possibly resulting in injury to both the user and the user's partner. Additionally, current penile supports are bulky, have large cross-sections and do not accommodate changes in penis size during erection. Current devices are often ineffective in retaining their contoured shape and expensive to manufacture due to their relatively complex designs.

SUMMARY

In one embodiment, the expandable external penile support device may include a first support ring positionable proximate a base of a penis, a latch pivotally coupled to the first support ring, and a support member extending from the latch and defining a second support ring engageable with a distal end of the penis and having an arcuate length. The arcuate length automatically varies according to changes in the penis diameter.

Another embodiment of the expandable external penile support device may include a first support ring positionable proximate a base of a penis, a latch pivotally coupled to the first support ring, a support member extending from the latch and defining a second support ring engageable with a distal end of the penis, and a slider coupled to and moveable along a length of the support member. The slider includes a compensation ring.

BRIEF DESCRIPTION OF THE DRAWINGS

FIG. 19 is a detailed section view of the support member in a flattened configuration taken along a horizontal plane (co-planar with the second support ring).

FIG. 20 is a section view of the support member in a flattened configuration taken along a horizontal plane (co-planar with the second support ring).

FIG. 21 is a section view of a non-erect penis glans area engaged by the second support ring in a flattened configuration taken along a horizontal plane (co-planar with the second support ring).

FIG. 33 is a top view of the wire core of FIG. 32 with an outer support ring included.

FIG. 34 is a top view of the supporting attachment in a flattened configuration.

FIG. 35 is a side view of the supporting attachment of FIG. 34.

FIG. 36 is a section view taken along lines 36-36 of FIG. 34.

FIG. 37 is a section view taken along lines 37-37 of FIG. 34.

FIG. 60 is a perspective view of the soft embodiment of the support member.

FIG. 61 is a section view taken along lines 61-61 of the FIG. 60.

FIG. 62 is an alternate embodiment of a connector.

DETAILED DESCRIPTION OF THE DRAWINGS

Figure 1:
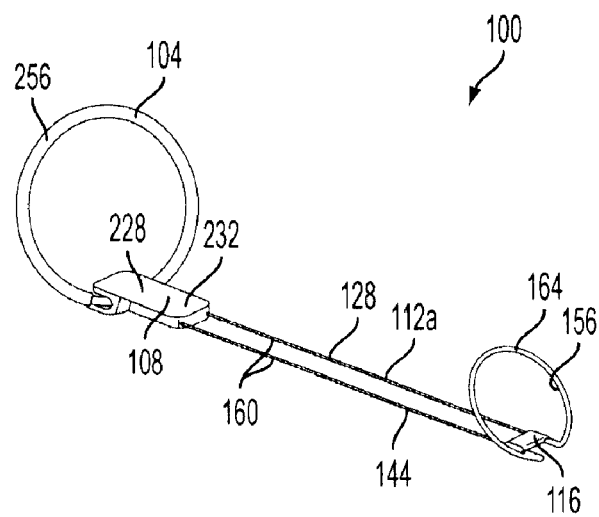
FIG. 1 is a perspective view of the expendable external penile support device (EEPSD).

It is to be understood that the invention is not limited in its application to the details of construction and the arrangements of the components set forth in the following description or embodiments, or illustrated in the drawings. The invention is capable of other embodiments and of being practiced or being carried out in various ways.

FIGS. 1-30, and 46-62 illustrate an expandable external penile support device (EEPSD) 100 to be placed on the penis to allow men to perform intercourse with a no or weak erection without the need for medications, surgeries, and the like. In addition, the EEPSD 100 may be used with men suffering from any one of, but not limited to, erectile dysfunction, premature ejaculation, and Peyronie's disease. The EEPSD 100 may also be used to overcome discrepancies between men and women's anatomy. The EEPSD 100 includes a first support ring 104, a latch 108 pivotably coupled to the first support ring 104, a support member 112a, b extending from the latch 108, and a sliding lock 116 coupled to and moveable along the support member 112a, b. The EEPSD 100 is flexible enough to accommodate both straight and bent penis shafts (see FIGS. 2 and 3), yet provide sufficient support to the penis to permit penetration of the penis for purposes of intercourse. In some constructions, the EEPSD 100 does not rotate on the penis during use. In other constructions, the EEPSD 100 applies uniform pressure to a vein of the penis for optimally stimulating and maintaining an erection.

In the present invention, the support member 112a, b of the EEPSD 100 may comprise a first semi-rigid embodiment 112a (see FIGS. 1-8), or a second soft embodiment 112b (see FIGS. 60-62). The semi-rigid embodiment 112a of the support member is adapted for use with patients that are unable to achieve erection. As such, the semi-rigid embodiment provides sufficient support for full penetration, even when a natural erection does not occur. In contrast, the soft embodiment 112b of the support member is designed for use with healthy men who can achieve full or partial erection and want to extend intercourse after ejaculation. The soft embodiment 112b provides a more discrete and comfortable design, but requires a sufficient level of blood flow in the penis to achieve penetration.

Illustrated in FIGS. 1-8, 19-24, 29-30, and 48-59, the semi-rigid embodiment 112a of the support member includes a first body member 120 having a first loop portion 124 with a first end 126 and a first support rod portion 128 extending from the first loop portion 124 to produce a first distal end 132 (FIG. 4), and a second body member 136 having a second loop portion 140 with a second end 142 and a second support rod 144 extending from the second loop portion 140 to produce a second distal end 148. The support member 112a further includes a spring 152, spanning between and coupled to (e.g., by welding) the first end 132 of the first body member 120 and to the second end 142 of the second body member 136, to produce a second support ring 156 (see FIG. 6). In some specific constructions, the spring 152 is attached such that when the spring 152 is in a rested position, there is a small gap 166 between the first end 132 of the first body member 120 and the second end 142 of the second body member 136. In the illustrated embodiment, the first body member 120 and the second body member 146 are substantially similar in size and shape to simplify manufacturing of the EEPSD 100.

The first and second support rods 128, 144 extend between the second support ring 156 and the latch 108 (described below). The length of the support rods 128, 144 substantially correspond with the overall length of the penis, and may be custom built, come in a set of standard sizes, or be adjustable to accommodate different penis sizes. The support rods 128, 144 (and in the illustrated embodiment, the first and second body members 120, 136) are formed from any rigid-flexible material that can overcome the resistance of penetration during intercourse while being sufficiently flexible to accommodate changes in penis curvature during intercourse. More specifically, the support rods 128, 144 can be formed from any one of, but not limited to, titanium, titanium alloys, and musical or stainless steel wire ranging from about 0.010" to about 0.120" in diameter, and is preferably 0.038" in diameter. In the illustrated embodiment, the support rods 128, 144 are at least partially covered by a protective sheathing or plastic tubing 160 (see FIG. 7) with the distal ends 132, 148 preferably uncovered and bent at an angle with respect to the first and second support rods 128, 136, respectively (see FIG. 8).

The spring 152 extends between the first end 126 of the first body member 120 and the second end 142 of the second body member 136 to provide flexibility to the semi-rigid embodiment of the support member 112a. The spring 152 is typically formed from 302 stainless steel, 306 stainless steel, or musical wire with a diameter ranging from about 0.010" to about 0.015". The spring 152 can typically withstand a load between 5-15 pounds of pull. In the illustrated embodiment, the spring 152 will stretch (e.g., increase in overall length) from a rested state as the penis grows during erection. This allows the first end 126 of the first body member 120 to move away from the second end 142 of the second body member 136, increasing the overall size of the second support ring 156 (see FIG. 22). The spring 152 also provides flexibility to allow the support member 112a to be more easily placed on the penis when putting on the EEPSD 100 (described below).

The second support ring 156 of the support member 112a includes an overall diameter generally corresponding to the diameter of the penis. During use, the second support ring 156 is at least partially received within a groove 162 inward of the penis glans 163. In the illustrated embodiment, the second support ring 156 is over-molded (e.g., with medical grade silicone) to produce a jacket 164 substantially encompassing the second support ring 156, spring 152, and at least a portion of the plastic tubing 160. The jacket 164 chemically bonds with the second support ring 156, spring 152, and plastic tubing 160 to seal the structure and create a unitary piece devoid of gaps and/or pockets that may accumulate debris and possibly bacterium (see FIG. 19). In some constructions, the jacket 164 may also include a plurality of stimulation bumps 170 for enhanced female stimulation.

The second support ring 156 also defines an arcuate length. The arcuate length extends generally along the first loop portion 124, the gap 166 between the first end 126 of the first body member 120 and the second end 142 of the second body member 136, and the second loop portion 140. In the illustrated embodiment, the arcuate length of the second support ring 156 automatically varies according to the diameter of the penis. As such, the arcuate length will increase as the spring 152 stretches or the first end 126 of the first body member 120 moves away from the second end 142 of the second body member 136.

Illustrated in FIGS. 60-62, the soft embodiment of the support member 112b includes a first support rod 168 having a first end 172 and a second end 176, a second support rod 180 having a third end 184 and a fourth end 188, and a soft support loop 192 coupled to the second end 176 of the first support rod 168 and the fourth end 188 of the second support rod 180.

The support rods 168, 180 of the soft embodiment 112b of the support member extend between the soft support loop 192 and the latch 108 (described below). The length of the support rods 168, 180 substantially correspond with the overall length of the penis, and may be custom built, come in standard sizes, or be adjustable to accommodate different sizes of the male anatomy. The support rods 168, 180 are formed from any rigid but flexible material that can permit penetration while being sufficiently flexible to accommodate changes in penis curvature during intercourse. More specifically, the support rods 168, 180 may be formed from any one of, but not limited to, titanium, titanium alloys, and musical or stainless steel wire ranging from about 0.010" to about 0.120" in diameter, and is preferably 0.038" in diameter. In the illustrated embodiment, the support rods 168, 180 are at least partially covered by a protective sheathing or plastic tubing 200.

The second end 176 of the first support rod 168 and the fourth end 188 of the second support rod 180 are each stamped to form an enlarged or coined end 204, typically in the shape of a trapezoid (see FIG. 61), or a sphere (see FIG. 62). The coined ends 204 produce an increased retention surface so that objects may be molded onto the wires without axially slipping off. In the illustrated embodiment, a connector 196 is molded over each coined end 204 and at least a portion of the tubing 200. The connector 196 includes a spherical portion 212 and a plurality of fin elements 216 extending radially outwardly from the connector 196. The connector 196 is configured to allow the soft support loop 192 to be molded onto the second and fourth ends 176, 188 of the support rods 168, 188 without being easily removed.

The soft support loop 192 is molded onto the connectors 196 to produce a substantially arcuate body portion 220 and a pair of end portions 222. In the illustrated embodiment, the end portions 222 encompass at least a portion of each connector 196, extending between the fins 216 to produce a joint able to withstand the forces of operation. The body portion 220 of the soft support loop 192 is open over at least a portion of its circumference to allow the loop 192 to expand with the penis as it grows in diameter during erection. In the present invention, the soft support loop 192 is formed from silicone, however in some alternate constructions, the soft support loop 192 may also include a flexible plastic core (not shown) to provide additional rigidity. In yet another construction, the soft support loop may include a plurality of stimulation bumps (not shown) to increase female stimulation.

For the sake of brevity, only the semi-rigid embodiment 112a of the support member will be referenced with respect to the remaining elements of the EEPSD 100. However, it is to be understood that the present invention may be configured for either embodiment 112a, 112b of the support member.

Illustrated in FIGS. 1, 9-10, and 13, the latch 108 of the EEPSD is over-molded onto the distal end(s) 132, 148 of the support member 112 to provide a pivotable interface with the first support ring 104. The latch 108 includes a body 228 having a front support 232 over-molded onto the distal end(s)

132, 148 of the support member 112a and a retaining recess 236 generally opposite the front support 232 to pivotally receive, and retain, at least a portion of the first support ring 104. In the illustrated embodiment, the latch 108 retains the first support ring 104 by a snap fit. However in alternate constructions, the first support ring 104 may be retained by a pin, retention member, and the like. In yet another construction, the latch 108 may include a locking member (not shown) to lock the first support ring 104 in place with respect to the body 228.

Figures 2, 3:
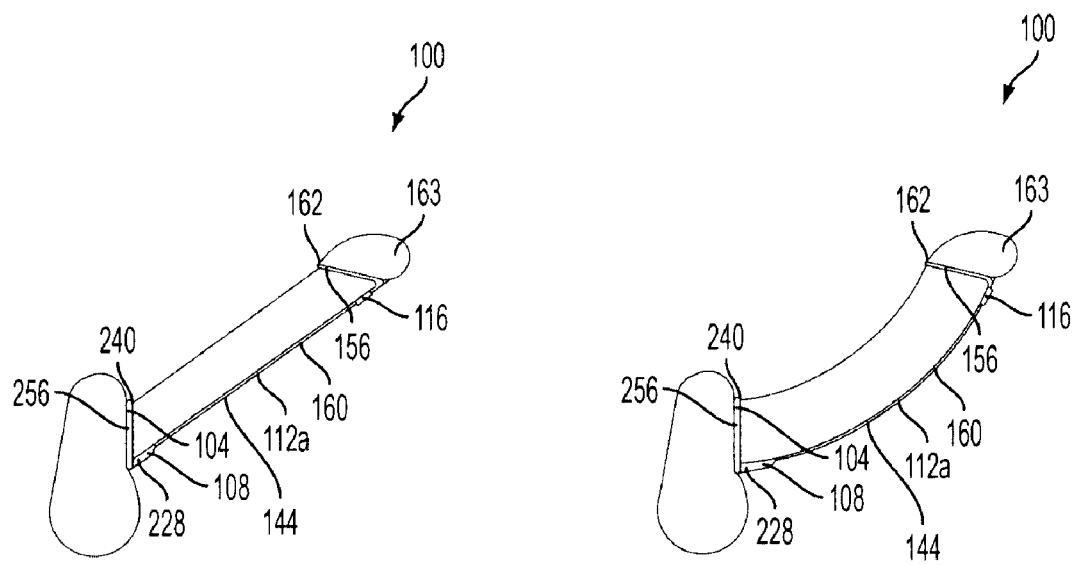
FIG. 2 is a side view of the EEPSD of FIG. 1 on a penis.
FIG. 3 is a side view of the EEPSD of FIG. 1. on a penis of a differing shape.
Figure 4:
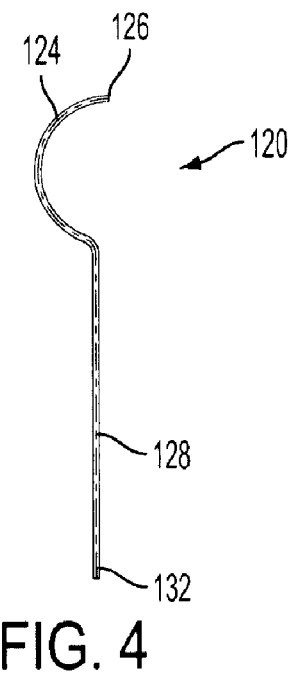
FIG. 4 is a top view of a first body member in a flattened configuration.
Figure 5:
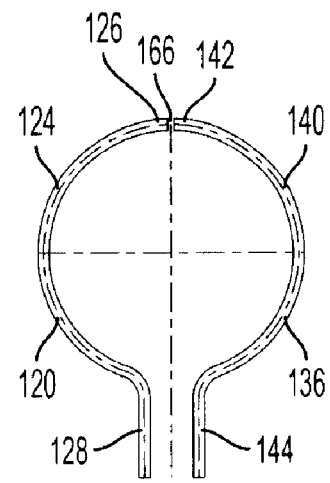
FIG. 5 is a top detailed view of a second support ring defined by a first body member and a second body member in a flattened configuration.
Figure 6:
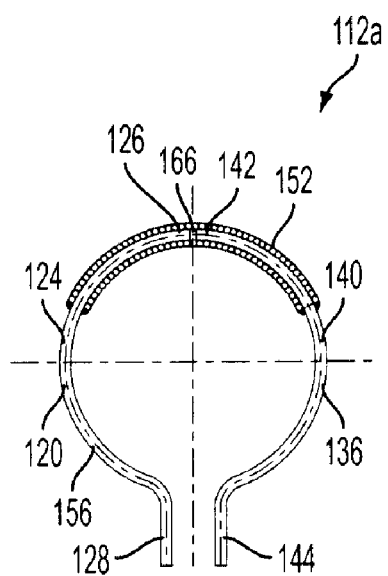
FIG. 6 is a detailed section view of the support member in a flattened configuration taken through a horizontal plane (co-planar with the second support ring).
Figure 7:
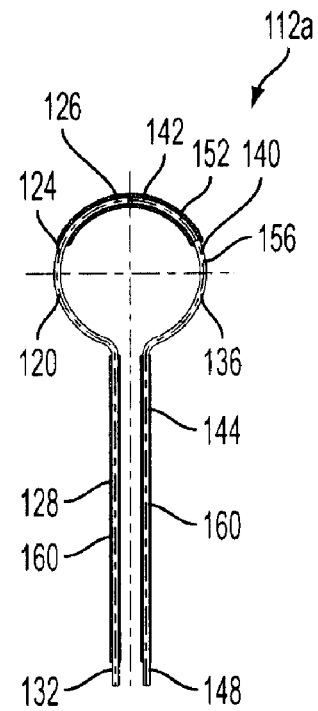
FIG. 7 is a section view of the first and second body members in a flattened configuration taken through a horizontal plane (co-planar with the second support ring) with the tubing added.
Figure 8:
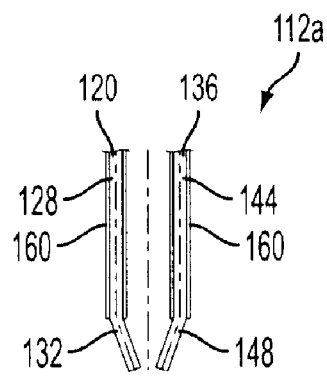
FIG. 8 is a detailed view of the distal ends of the first and second body members.
Figure 9:
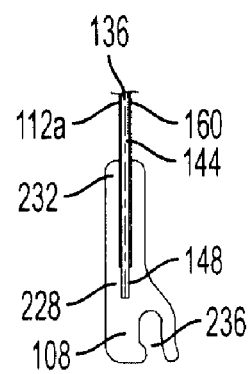
FIG. 9 is a section view of the latch taken along a vertical plane through the first support rod.
Figure 10:
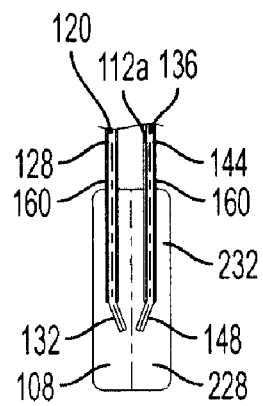
FIG. 10 is a section view of the latch taken along a horizontal plane through the first and second support rods.
Figure 11:
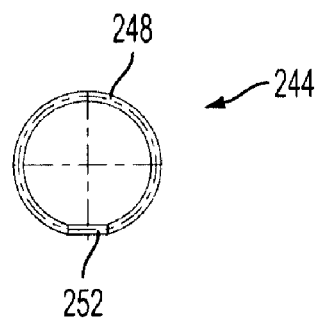
FIG. 11 is a top view of the inner core of the first support ring.
Figure 12:
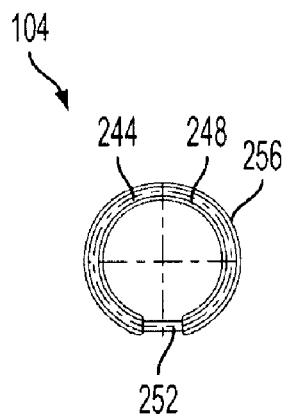
FIG. 12 is a section view of the first support ring taken through a horizontal plane (co-planar with the first support ring).
Figure 13:
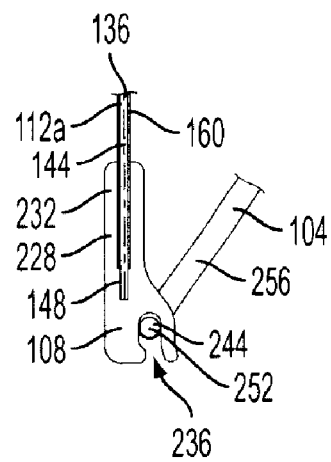
FIG. 13 is the section view of FIG. 9 showing the first support ring received by the latch.
Figure 14:
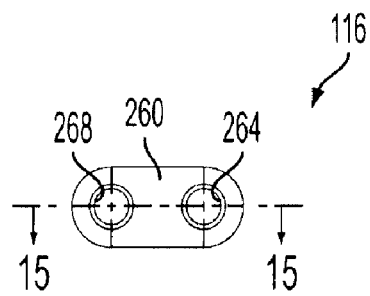
FIG. 14 is a front view of a body of a sliding lock.
Figure 15:
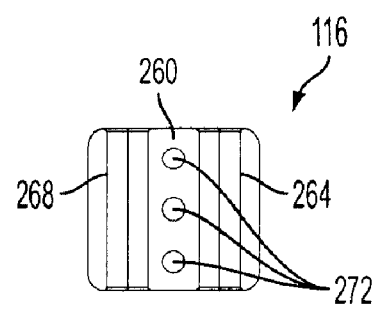
FIG. 15 is a section view taken along lines 15-15 of FIG. 14.
Figure 16:
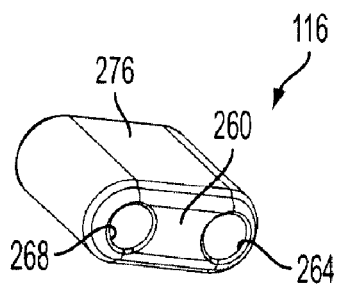
FIG. 16 is a top perspective view of the sliding lock.
Figure 17:
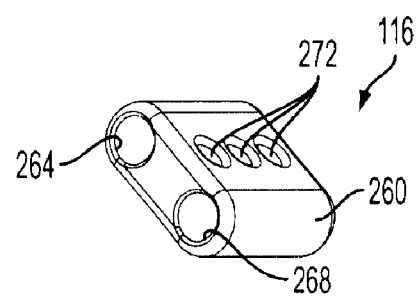
FIG. 17 is a bottom perspective view of the body of the sliding lock of FIG. 14.
Figure 18:
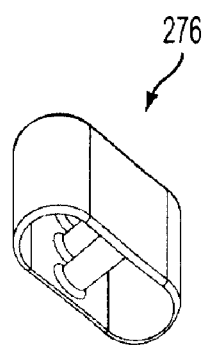
FIG. 18 is a perspective view of a silicone jacket for use on the body of the sliding lock of FIG. 14.
Figure 22:
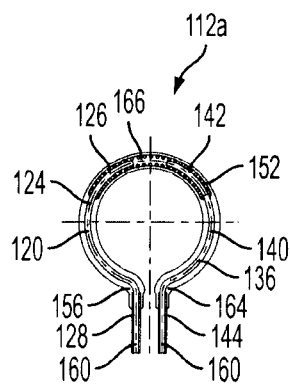
FIG. 22 is a detailed section view of the support member in a flattened configuration showing increased gap between the two loop components to accommodate an enlarged penis diameter during erection taken along a horizontal plane (coplanar with the second support ring).
Figure 23:
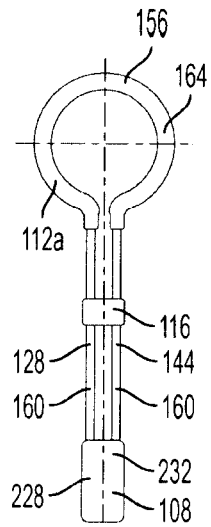
FIG. 23 is a top view of the EEPSD in a flattened configuration without the first support ring attached.
Figure 24:
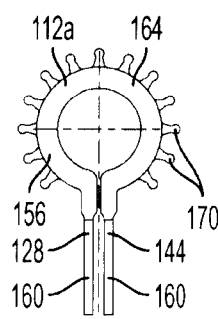
FIG. 24 is a detailed view of the EEPSD in a flattened configuration showing the second support ring with stimulation bumps.
Figure 25:
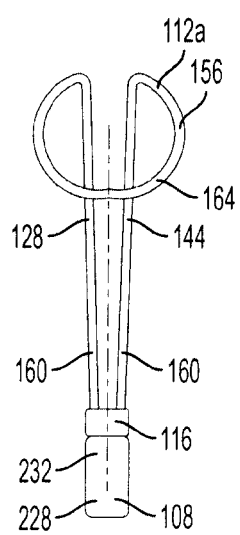
FIG. 25 is a top view of the EEPSD with the sliding lock positioned proximate the latch and the second support ring expanded.
Figure 26:
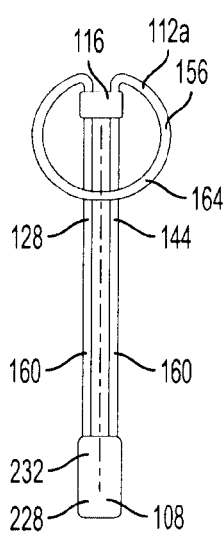
FIG. 26 is a top view of the EEPSD with the sliding lock positioned proximate the second support ring.
Figure 27:
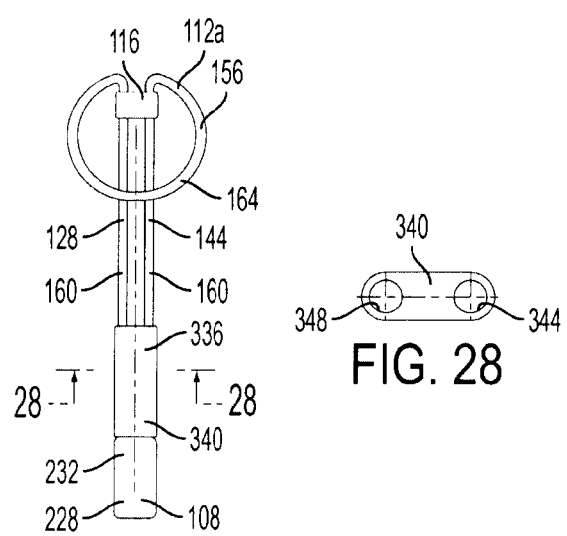
FIG. 27 is a top view of the EEPSD with a sliding attachment.
Figure 28:
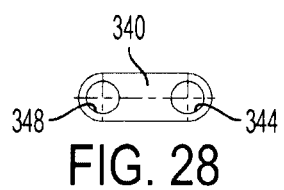
FIG. 28 is section view taken along line 28-28 of FIG. 27.
Figure 29:
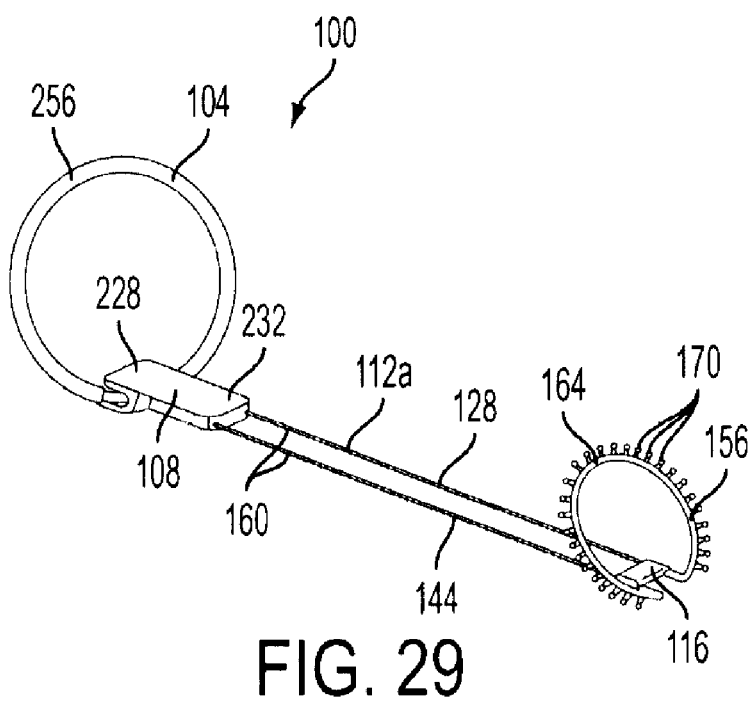
FIG. 29 is a perspective view of the EEPSD with stimulation bumps.
Figure 30:
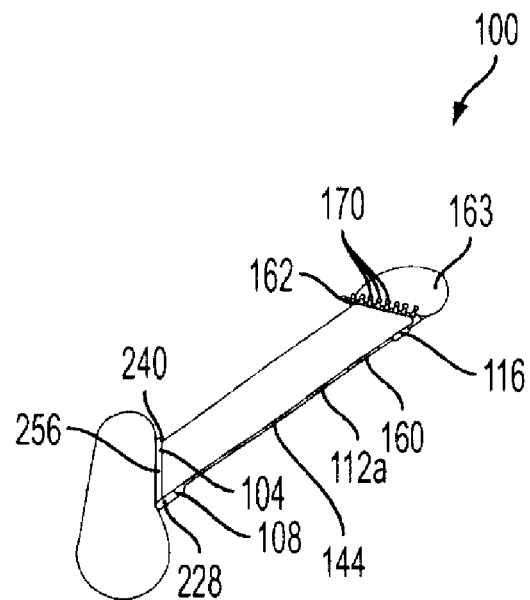
FIG. 30 is a side view of the EEPSD of FIG. 29 on a penis.
Figure 31:
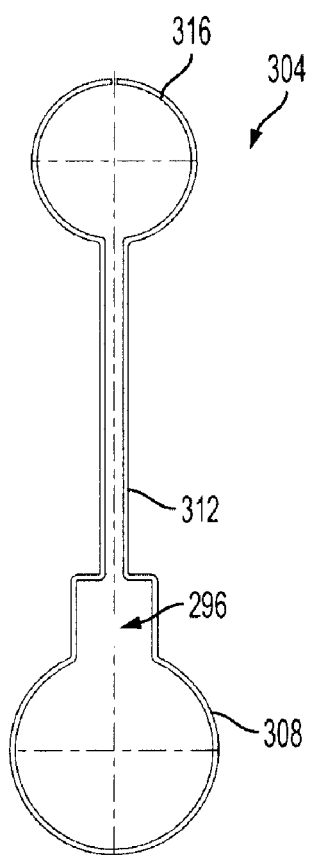
FIG. 31 is a top view of the wire core of a supporting attachment in a flattened configuration for use on the EEPSD.
Figure 32:
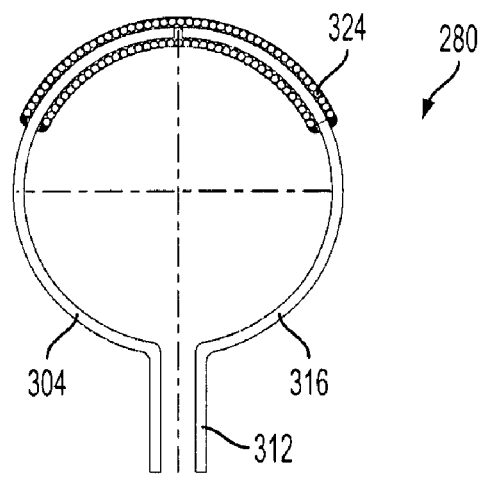
FIG. 32 is a detailed section view of the wire core in a flattened configuration with an added spring taken along a horizontal plane (co-planar with the stimulator ring).
Figure 38:
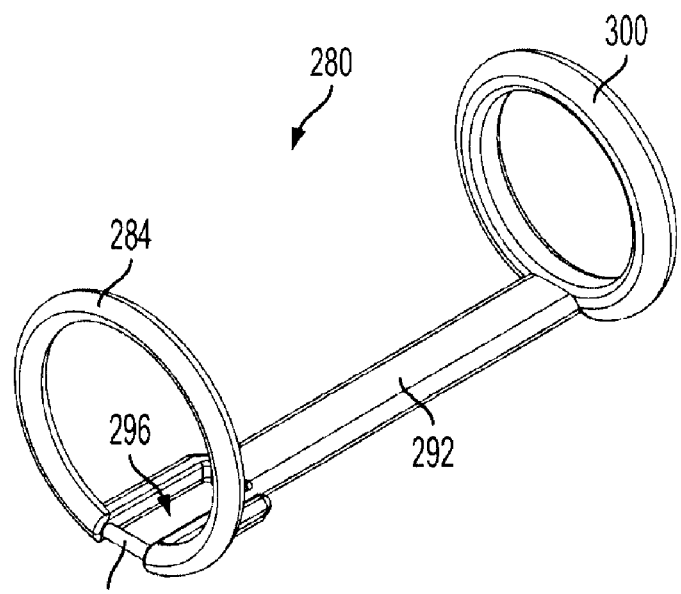
FIG. 38 is a perspective view of the supporting attachment.
Figure 39:
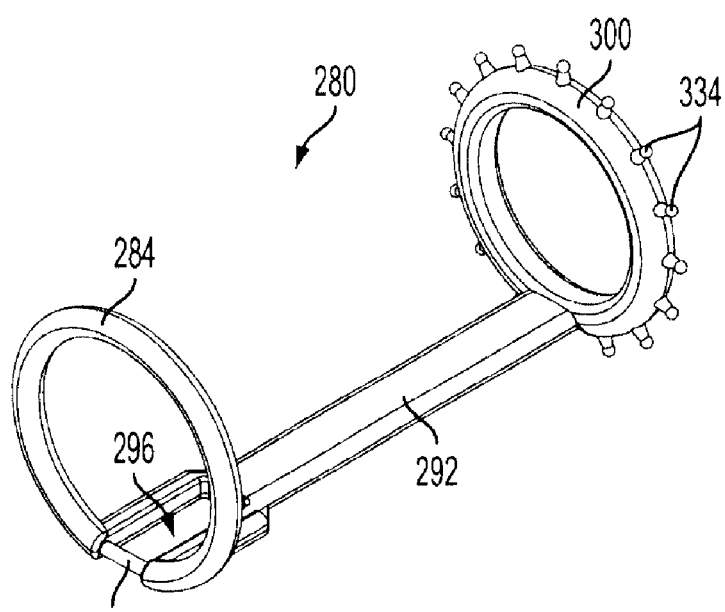
FIG. 39 is a perspective view of the supporting attachment with stimulation bumps.
Figure 40:
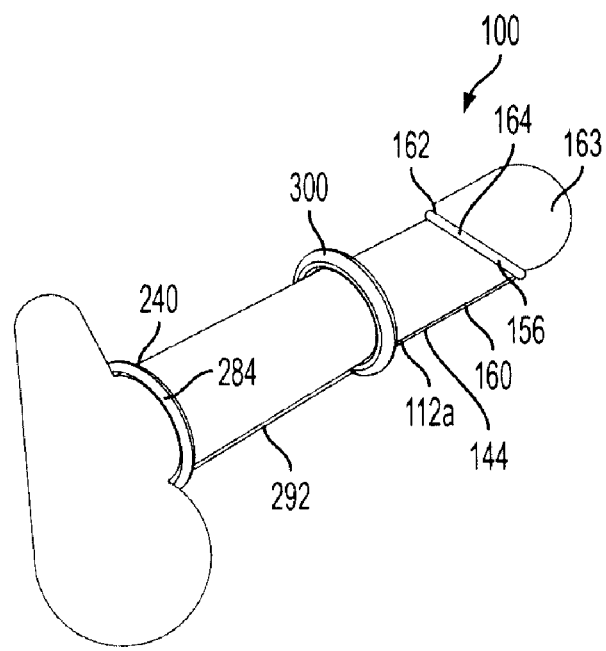
FIG. 40 is a side view of the EEPSD with the supporting attachment of FIG. 38, all placed on a penis.
Figure 41:
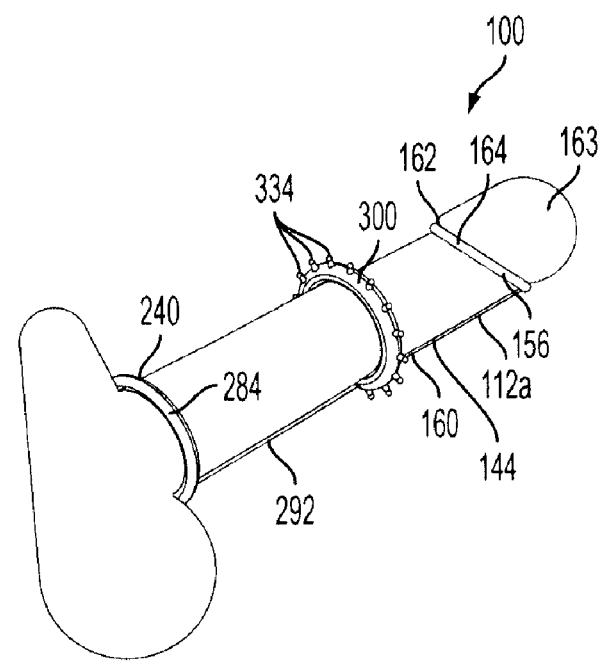
FIG. 41 is a side view of the EEPSD with the supporting attachment of FIG. 39, all placed on a penis.
Figure 42:
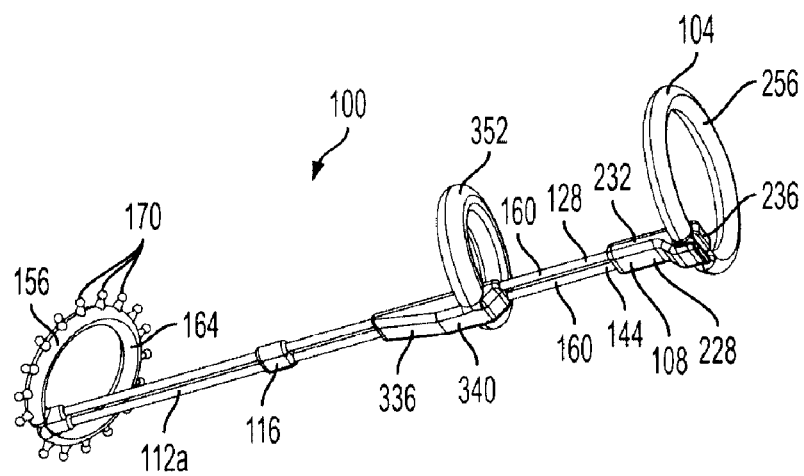
FIG. 42 is a bottom perspective view of the EEPSD with a sliding attachment.
Figure 43:
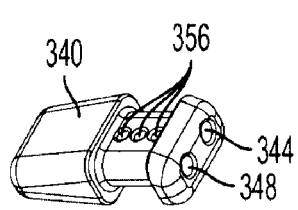
FIG. 43 is a perspective view of a base of the sliding attachment.

Illustrated in FIGS. 1, 11, and 12, the first support ring 104 is placed near the base 240 of the penis to "anchor" the EEPSD 100 during operation. The first support ring 104 includes an inner core 244 typically formed of plastic having an arcuate portion 248 and a linear portion 252, and a jacket 256 encompassing at least a portion of the inner core 244. More specifically, the arcuate portion 248 of the inner core 244 includes an inner diameter substantially corresponding to the diameter of the base 240 of the penis, and the linear portion 252 of the inner core 244 is configured to be at least partially received by and pivotable with respect to the latch 108. The linear portion 252 may also include a plurality of flat surfaces (not shown) corresponding to predetermined positions between the first support ring 104 and the latch 108.

Illustrated in FIGS. 1, 14-18, 23, 25-27, and 48-53, the sliding lock 116 is coupled to and moveable along the support member 112a. The sliding lock 116 may be positioned along the length of the support member 112a to adjust the tension or tightness the second support ring 156 exerts onto the penis. In the illustrated embodiment, when the sliding lock 116 is placed proximate the latch 108, the second support ring 156 loosely fits onto the penis (see FIG. 25). However, as the sliding lock 116 is moved towards the second support ring 156, the second support ring becomes increasingly smaller in diameter, resulting in a tighter, more secure fit (see FIG. 26).

The sliding lock 116 includes a body 260 having a first channel 264 and a second channel 268 parallel to and spaced a distance from the first channel 264 substantially corresponding to the distance between the first and second support rods 128, 144. The sliding lock 116 further includes one or more recesses 272 defined by the body 260, and a jacket 276 (e.g., molded from silicone) at least partially received by the recesses 272 and substantially encompassing the body 260. In the illustrated construction, the diameters of the first and second channels 264, 268 substantially correspond with the outer diameter of the tubing 160 to allow the sliding lock 116 to slide along the support rods 128, 144 yet maintain its position once in place. In some alternate constructions, the sliding lock 116 may include a locking member (not shown) to lock the sliding lock 116 with respect to the support member 112.

Illustrated in FIGS. 31-41, a first support attachment 280 may be used in place of the first support ring 104. When installed on an EEPSD 100, the support attachment 280 reinforces the support member 112 and provides additional stiffening support to the penis when compared to using only the first support ring 104. More specifically, the support attachment 280 is typically utilized in EEPSD's 100 exceeding 6" in length. The support attachment 280 includes a third support ring 284 having a support bar 288 to be received by the latch 108, a bridge 292 extending from the third support ring 284 having a cavity 296 to at least partially receive the latch 108, and a stimulator ring 300 coupled to the bridge 292 substantially opposite the third support ring 284.

FIGS. 31-34 illustrate the support attachment 280 in greater detail. The support attachment 280 further includes a wire core 304 bent to produce a support ring portion 308, a bridge portion 312, and a stimulator ring portion 316 (see FIG. 31), where after subsequent manufacturing processes, each portion will generally define the shape of the third support ring 284, the bridge 292, and the stimulator ring 300, respectively. In the illustrated construction, the support ring portion 308 is over-molded with plastic to create an outer support ring 320 and the support bar 288 (see FIG. 33). Similar to the semi-rigid embodiment 112a, a spring 324 extends between and is coupled to the ends of the wire core 304 to allow the stimulator ring portion 316 to adjust to changes in penis diameter due to erection. The wire core 304/outer support ring 320 assembly is then over-molded (e.g., with silicone) to produce a jacket 328 substantially encompassing the support attachment 280 (see FIG. 34). In the illustrated construction, the support attachment 280 is formed from a single piece of wire, however in some alternate constructions more than one wire may be used and coupled together.

In some alternate constructions, the support attachment 280 is formed by bending the wire core 304 in a first plane (e.g., horizontally) to produce a flattened configuration, over-molding the necessary portions with silicone, and then bending the wire core 304 in a second plane non-parallel to the first plane (e.g., vertically). In yet other constructions, the stimulator ring 300 may also include a plurality of stimulation bumps 334 (see FIG. 39).

The bridge 312 of the support attachment 280 is configured to properly position the support attachment 280 with respect to support member 112a. In the illustrated construction, the bridge includes a cross-sectional shape having a pair of downwardly extending walls 332 (see FIGS. 36 and 37). The walls 332 engage the outer portions of the support rods 128, 144 to limit the amount of relative lateral motion that may occur between the support attachment 280 and the support member 112a. In some alternate constructions, the bridge 312 may include a retaining member (not shown) to "snap-fit" the bridge 312 to the support rods 128, 144. In yet another construction, the bridge 312 may at least partially enclose the support rods 128, 144 to limit relative rotation between the two members 112a, 312.

FIGS. 42-45 illustrate a second sliding attachment 336 for use on the EEPSD 100. The sliding attachment 336 serves as a compensation device to overcome discrepancy in sizes of genitalia between males and females. In other words, the second sliding attachment 336 may act as a non-surgical alternative for penis enlargement. The sliding attachment 336 includes a base 340 having a first and a second channel 344, 348 each corresponding to a respective support rod 128, 144, and a compensation ring 352 extending from the base to substantially encompass a portion of the penis. The sliding attachment 336 is positionable along the length of the support member 112a during intercourse to provide the feel of an enlarged penis diameter.

The channels 344, 348 of the base 346 include a diameter substantially corresponding to the outer diameter of the tubing 160. The channels 344, 348 are configured to allow the sliding attachment 336 to slide along the support rods 128, 144 yet providing sufficient friction to maintain the sliding attachment 336 in its location during intercourse. In the illustrated embodiment, the base 346 may also include a plurality of recesses 356 to better secure the ring 352 and/or silicone coating (described below) to the base. In an alternate construction, the base 364 may include a retention member (not shown) to lock the sliding attachment 336 in position with respect to the support portion 112a.

Figure 44:
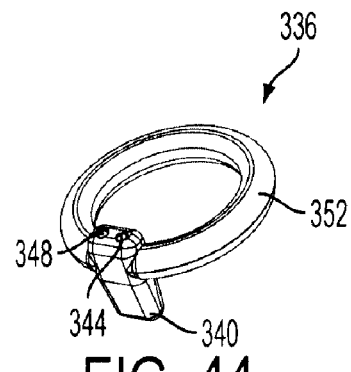
FIG. 44 is a bottom perspective view of the sliding attachment.
Figure 45:
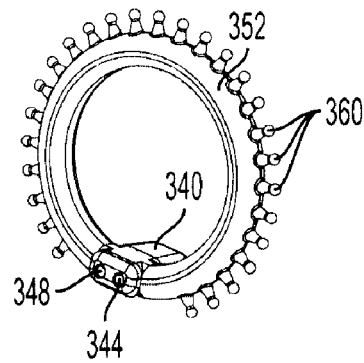
FIG. 45 is a top perspective view of the sliding attachment with stimulation bumps.
Figure 46:
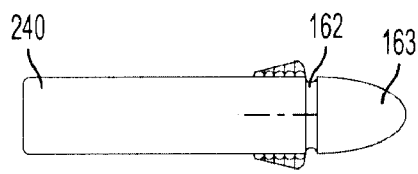
FIG. 46 is a side view of a penis with skin pulled back to expose a groove.
Figure 47:
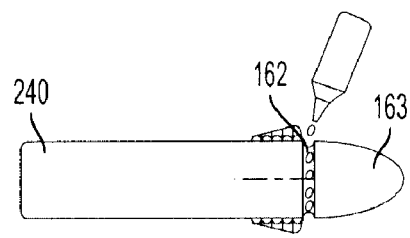
FIG. 47 is a side view of applying lubrication to the groove of the penis.
Figure 48:
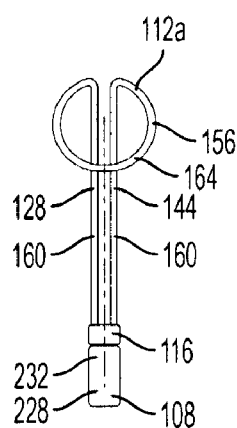
FIG. 48 is a top view of the EEPSD with sliding lock proximate the latch.
Figure 49:
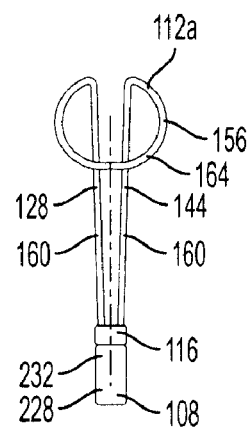
FIG. 49 is a top view of the EEPSD with the second support ring stretched open.
Figure 50:
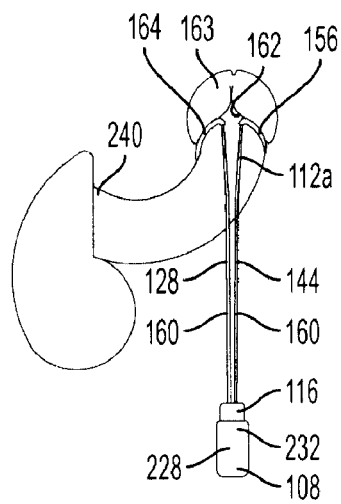
FIG. 50 is a view of the second support ring being placed in the groove behind the penis glans.
Figure 51:
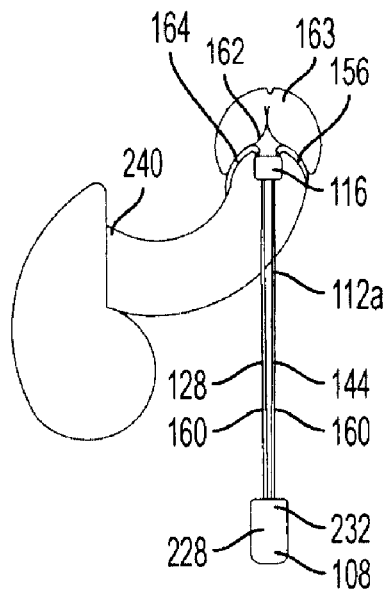
FIG. 51 is a view of the EEPSD on a penis with the sliding lock adjacent the second support ring.
Figure 52:
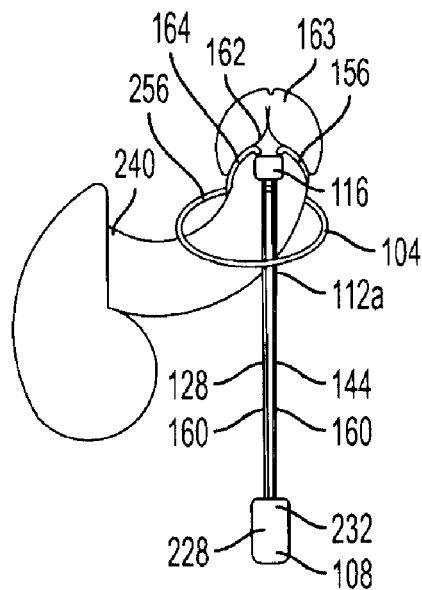
FIG. 52 is a view of the EEPSD on a penis with the first support ring being placed on the penis.
Figure 53:
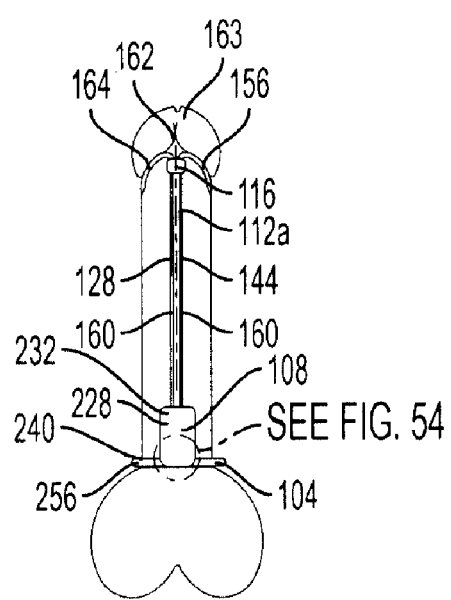
FIG. 53 is a bottom view of the EEPSD placed on the penis.
Figure 54:
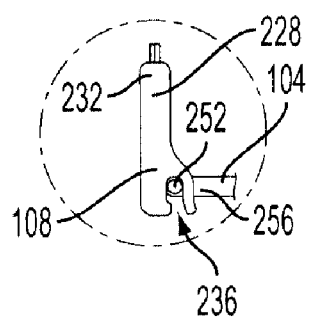
FIG. 54 is a detailed side view of the first support ring of FIG. 53 being received by the latch.
Figure 55:
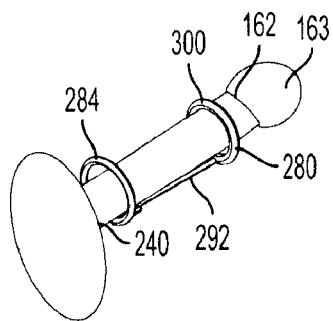
FIG. 55 is a side view of the support attachment placed on a penis.
Figure 56:
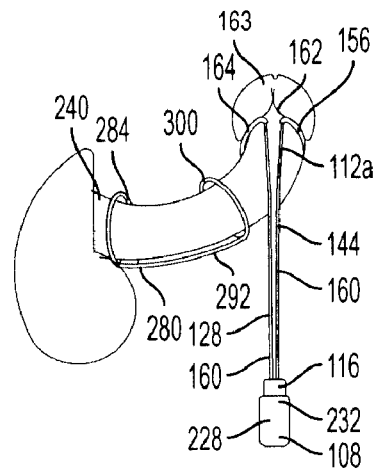
FIG. 56 is a side view of the support attachment placed on a penis and the second support ring being placed in the groove behind the penis glans.
Figure 57:
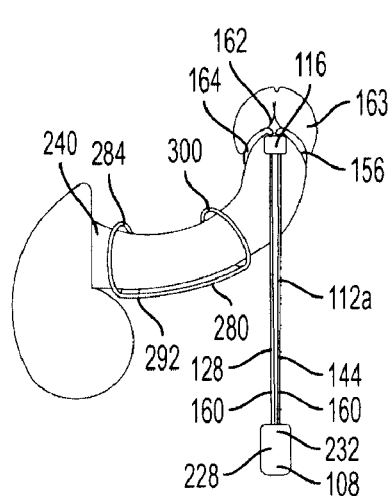
FIG. 57 is a side view of the support attachment placed on a penis and the sliding lock adjacent the second support ring.
Figure 58:
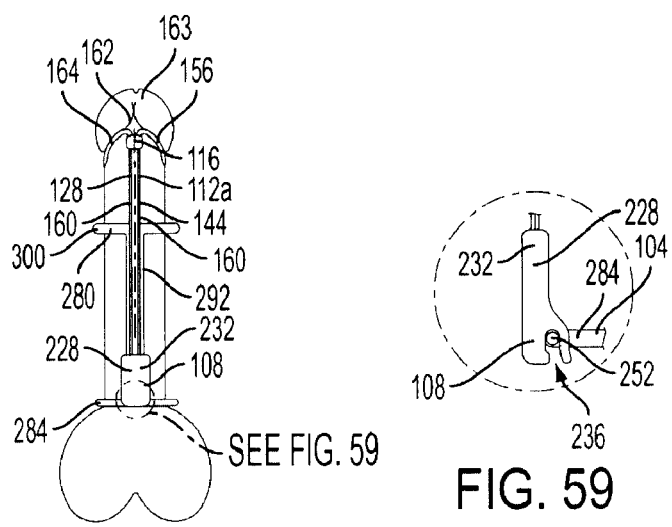
FIG. 58 is a bottom view of the EEPSD with support attachment placed on a penis.
Figure 59:
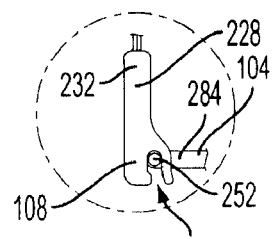
FIG. 59 is a detailed side view of the support attachment being received by the latch.

In the illustrated construction, the compensation ring 352 of the sliding attachment 336 is generally molded (e.g., with silicone) onto the base 346 (see FIG. 44). However, in alternate constructions, the ring 352 may be removeably coupled to and interchangeable with the base 346. In yet other alternate constructions, the ring 352 may include one or more stimulation bumps 360 for greater female stimulation.

In the present invention, the EEPSD 100 and the related attachments 280 and 336 are each substantially coated (or jacketed) with a layer of medical grade silicone to provide antimicrobial agents and a coefficient of friction that is equal to or less than penile skin or the skin of the partner. Further, the coating of each unit helps eliminate any gaps in the structures that may accumulate debris or promote bacterium growth. In some constructions, the EEPSD 100 is formed from only non-corrosive FDA approved materials. In addition, each element is substantially unitary and unable to be disassembled.

The following are steps for placing the EEPSD 100 on a penis. Retract skin back from the penis glans 163 and groove 162 (see FIG. 46). Apply lubricant to groove 162 as necessary (see FIG. 47). Position the sliding lock 116 proximate the latch 108 (see FIG. 48). Stretch the second support ring 156 open to accommodate the penis glans 163 (see FIG. 49). Place second support ring 156 around the penis glans 163 and into groove 162 (see FIG. 50). Shift the sliding lock 116 towards the second support ring 156 until second support ring 156 is securely in the groove 162 (see FIG. 51). Place the first support ring 104 (or support attachment 280 when in use) near the base 240 of the penis (see FIG. 52). Pivotably couple the first support ring 104 and the latch 108 (see FIGS. 53 and 54).

The EEPSD 100 may be manufactured and assembled as follows. Bend a piece of wire in a first plane (e.g., horizontally) to produce the first body member 120 (see FIG. 4) in a substantially flattened configuration. Bend a second wire in the first plane to produce a second body member 136 substantially identical the first body member 120. Couple (e.g., weld) the spring 152 between the first end 126 of the first body member 120 and the second end 142 of the second body member 136 to produce the support member 112a and second support ring 156 (see FIG. 6) in a substantially flattened configuration. Substantially cover the first and second support rods 128, 144 with a piece of plastic tubing 160 (see FIG. 7). Over-mold the second support ring 156 (e.g., with silicone) to create a jacket 164 substantially encompassing the second support ring 156, the spring 152, and at least a portion of the tubing 160 (see FIG. 19). Bend the second support ring 156 in a second plane non-parallel to the first plane (e.g., vertically) between about 90 to about 135 degrees. Position the sliding lock 116 onto the first and second support rods 128, 144 (see FIG. 20). Over-mold the latch 108 onto the distal ends 132, 148 of the support member 112a (see FIG. 23). Pivotably couple the first support ring 104 to the latch 108 (see FIG. 1).

Alternately, the EEPSD 100 utilizing the soft embodiment 112b of the support member may be assembled as follows. Stamp or coin the second end 172 of the first support rod 168 and the fourth end 188 of the second support rod 180. Substantially cover the first and second support rods 168, 180 with a piece of plastic tubing 200. Over-mold the connector 196 onto the coined ends 204 of the support rods 168, 180 (see FIGS. 61 and 62). Over-mold the soft support loop 192 onto the joints 108 (see FIG. 60). Over-mold the latch 108 onto the distal ends 132, 148 of the support member 112a. Pivotably couple the first support ring 104 to the latch 108.

What is claimed is:

1. An expandable external penile support device for use on a penis having a base, a distal end, and a variable diameter, the expandable external penile support device comprising:
 a first support ring positionable proximate the base of the penis;
 a latch pivotably coupled to the first support ring; and
 a support member extending from the latch and defining a second support ring engageable with the distal end of the penis and having an arcuate length, where the arcuate length of the second support ring automatically varies according to the diameter of the penis,
 wherein the support member includes a first body member having a first loop portion with a first end, a second body member having a second loop portion with a second end, and a spring member coupled between the first end and the second end.

2. The expandable external penile support device of claim 1, wherein the second support ring is of sufficient size to substantially encircle the distal end of the penis.

3. The expandable external penile support device of claim 1, wherein the second support ring includes a flexible silicone body member.

4. The expandable external penile support device of claim 1, further comprising a sliding lock positionable along the length of the support member to adjust the diameter of the second support ring.

5. The expandable external penile support device of claim 4, wherein the sliding lock is at least partially coated with a silicone jacket.

6. The expandable external penile support device of claim 1, wherein at least a portion is coated in material having a coefficient of friction equal to or less than that of penile skin.

7. The expandable external penile support device of claim 1, wherein at least a portion of the expandable external penile support device includes a plurality of stimulation bumps.

8. The expandable external penile support device of claim 1, further comprising a layer of material substantially coating the device.

9. An expandable external penile support device for use on a penis having a base and a distal end, the expandable external penile support device comprising:
 a first support ring positionable proximate the base of the penis;
 a latch pivotably coupled to the first support ring;
 a support member extending from the latch and defining a second support ring engageable with the distal end of the penis; and
 a slider coupled to and moveable along a length of the support member, the slider including a compensation ring,
 wherein the support member includes a first body member having a first loop portion with a first end, a second body member having a second loop portion with a second end, and a spring member coupled between the first end and the second end.

10. The expandable external penile support device of claim 9, wherein the support member includes one or more support rods, and wherein the slider includes one or more channels each configured to receive a support rod of the one or more support rods.

11. The expandable external penile support device of claim 9, wherein at least a portion of the device includes a plurality of stimulation bumps.

12. The expandable external penile support device of claim 9, wherein at least a portion is coated in a material having a coefficient of friction equal to or less than that of penile skin.

13. The expandable external penile support device of claim 9, wherein at least one of the first support ring, the second support ring, and the compensation ring are expandable.

14. An expandable external penile support device for use on a penis having a base, a distal end, and a variable diameter, the expandable external penile support device comprising:
- a first support ring positionable proximate the base of the penis;
- a latch pivotably coupled to the first support ring; and
- a support member extending from the latch and defining a second support ring engageable with the distal end of the penis and having an arcuate length, where the arcuate length of the second support ring automatically varies according to the diameter of the penis, wherein the support member includes at least one support rod extending from the latch and has a coined end, wherein the coined end is over-molded with material to produce a connector, and wherein an end of the second support ring is molded onto the connector.

* * * * *